United States Patent
Fortuna et al.

(10) Patent No.: US 11,510,635 B2
(45) Date of Patent: Nov. 29, 2022

(54) RADIOLOGICAL IMAGING DEVICE

(71) Applicant: Epica International, Inc., San Clemente, CA (US)

(72) Inventors: Damiano Fortuna, Rignano Sull'Arno (IT); Leonardo Manetti, Montevarchi (IT); Denis De Micheli, Navacchio di Cascina (IT)

(73) Assignee: EPICA INTERNATIONAL, INC., San Clemente, CA (US)

( * ) Notice: Subject to any disclaimer, the term of this patent is extended or adjusted under 35 U.S.C. 154(b) by 0 days.

(21) Appl. No.: 17/020,763

(22) Filed: Sep. 14, 2020

(65) Prior Publication Data

US 2021/0000432 A1    Jan. 7, 2021

Related U.S. Application Data

(63) Continuation of application No. 16/073,773, filed as application No. PCT/IB2017/050438 on Jan. 27, 2017, now Pat. No. 10,772,577.

(30) Foreign Application Priority Data

Feb. 1, 2016   (IT) .......................... UB2016A000047

(51) Int. Cl.
  *G06K 9/00*    (2022.01)
  *A61B 6/03*    (2006.01)
  (Continued)

(52) U.S. Cl.
  CPC ............ *A61B 6/032* (2013.01); *A61B 6/0407* (2013.01); *A61B 6/4405* (2013.01); *A61B 34/30* (2016.02);
  (Continued)

(58) Field of Classification Search
  CPC ..... A61B 6/4405; A61B 6/032; A61B 6/0407; A61B 34/30; A61B 2090/376;
  (Continued)

(56) References Cited

U.S. PATENT DOCUMENTS 5,142,930 A    9/1992  Allen et al.
5,386,453 A *  1/1995  Harrawood .......... A61B 6/0442
                                              378/196

(Continued)

FOREIGN PATENT DOCUMENTS

CN    1522673 A    8/2004
CN    1694647 A    11/2005

(Continued)

OTHER PUBLICATIONS

Written Opinion and Search Report from Italian Patent Application No. UB20160047, 8 pages, dated Sep. 18, 2016.

(Continued)

*Primary Examiner* — Shervin K Nakhjavan
(74) *Attorney, Agent, or Firm* — Steptoe & Johnson LLP; Carl B. Wischhusen

(57) ABSTRACT

A radiological imaging device includes a gantry configured to perform radiological imaging and defining an area of analysis, a bearing structure supporting the gantry, and a robotic arm configured to move a medical instrument with respect to the area of analysis. The bearing structure includes a guide defining a translation axis substantially parallel to a longitudinal axis of the device, a first carriage connected to the gantry, and a second carriage connected to said robotic arm, the first and second carriages moving independently of each other, said gantry and said robotic arm configured to move along said translation axis.

13 Claims, 9 Drawing Sheets

(51) Int. Cl.
*A61B 6/04* (2006.01)
*A61B 6/00* (2006.01)
*A61B 34/30* (2016.01)
*A61B 90/00* (2016.01)

(52) U.S. Cl.
CPC . *A61B 2090/376* (2016.02); *A61B 2090/3762* (2016.02)

(58) Field of Classification Search
CPC .......... A61B 2090/3762; A61B 6/4435; A61B 6/547; A61B 6/035; A61B 34/20; A61B 6/4452; A61B 6/54; A61B 6/00; A61B 6/027; A61B 6/4458; A61B 34/00; A61B 34/32; A61N 5/1049; A61N 5/1081; A61N 5/1083; G21K 5/10
See application file for complete search history.

(56) References Cited

U.S. PATENT DOCUMENTS

| | | | | |
|---|---|---|---|---|
| 6,058,323 | A * | 5/2000 | Lemelson | A61B 17/320758 128/925 |
| 6,435,713 | B1 * | 8/2002 | Iizuka | A61B 6/4441 378/197 |
| 7,441,953 | B2 * | 10/2008 | Banks | A61B 5/1038 378/197 |
| 9,039,282 | B2 * | 5/2015 | Maschke | A61B 6/4464 378/197 |
| 9,259,195 | B2 * | 2/2016 | Yanof | A61B 90/50 |
| 2002/0039403 | A1 * | 4/2002 | Oota | A61B 6/5235 378/196 |
| 2002/0080921 | A1 * | 6/2002 | Smith | A61B 6/4464 378/189 |
| 2002/0087065 | A1 | 7/2002 | Yanof et al. | |
| 2003/0091156 | A1 * | 5/2003 | Crain | A61B 6/547 378/197 |
| 2003/0097060 | A1 | 5/2003 | Yanof et al. | |
| 2003/0128801 | A1 * | 7/2003 | Eisenberg | A61B 6/032 378/19 |
| 2004/0034438 | A1 * | 2/2004 | Uematsu | A61N 5/1049 700/59 |
| 2004/0184579 | A1 * | 9/2004 | Mihara | A61B 6/548 378/65 |
| 2005/0041775 | A1 * | 2/2005 | Batzinger | G01N 23/18 378/59 |
| 2005/0075563 | A1 * | 4/2005 | Sukovic | G16H 50/50 600/427 |
| 2006/0149147 | A1 | 7/2006 | Yanof | |
| 2007/0013336 | A1 * | 1/2007 | Nowlin | A61B 90/37 318/568.21 |
| 2008/0004523 | A1 | 1/2008 | Jensen | |
| 2008/0247506 | A1 | 10/2008 | Maschke | |
| 2009/0248038 | A1 * | 10/2009 | Blumenkranz | B25J 13/085 606/130 |
| 2010/0274120 | A1 * | 10/2010 | Heuscher | A61B 6/032 600/424 |
| 2011/0085636 | A1 * | 4/2011 | Dennerlein | A61B 6/032 378/4 |
| 2011/0210261 | A1 * | 9/2011 | Maurer, Jr. | A61B 6/025 250/393 |
| 2014/0153696 | A1 * | 6/2014 | Behling | H01J 35/02 378/62 |
| 2014/0163736 | A1 | 6/2014 | Azizian et al. | |
| 2014/0275953 | A1 * | 9/2014 | Gregerson | A61B 6/4405 600/407 |
| 2015/0117604 | A1 * | 4/2015 | Chrost | H01J 35/103 378/62 |
| 2015/0150525 | A1 | 6/2015 | Navab et al. | |
| 2015/0208993 | A1 | 7/2015 | Stoutenburgh et al. | |
| 2015/0352376 | A1 * | 12/2015 | Wiggers | A61B 6/587 250/252.1 |
| 2016/0128653 | A1 * | 5/2016 | Fortuna | A61B 6/4447 378/12 |
| 2016/0302871 | A1 * | 10/2016 | Gregerson | A61B 90/39 |

FOREIGN PATENT DOCUMENTS

| | | |
|---|---|---|
| CN | 1778275 A | 5/2006 |
| CN | 1969754 A | 5/2007 |
| CN | 101217913 A | 7/2008 |
| CN | 203436381 U | 2/2014 |
| CN | 105011957 A | 11/2015 |
| CN | 105050527 A | 11/2015 |
| CN | 204909474 U | 12/2015 |
| EP | 0934730 A1 | 8/1999 |
| WO | 2009/083851 A1 | 7/2009 |
| WO | 2015/052719 A1 | 4/2015 |
| WO | 2015/112424 A1 | 7/2015 |

OTHER PUBLICATIONS

Written Opinion and Search Report from Italian Patent Application No. UB20160102, 8 pages, dated Sep. 21, 2016.
First Search Report from Chinese Patent Application No. 201780022524.2, 2 pages, dated Aug. 12, 2021.
First Office Action from Chinese Patent Application No. 201780022524.2, 8 pages, dated Aug. 20, 2021.
Supplementary Search Report from Chinese Patent Application No. 201780022524.2, 2 pages, dated Feb. 5, 2022.

* cited by examiner

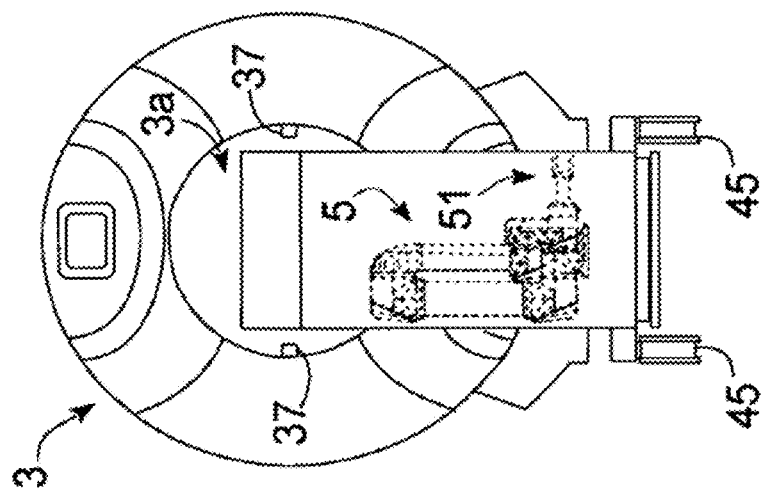
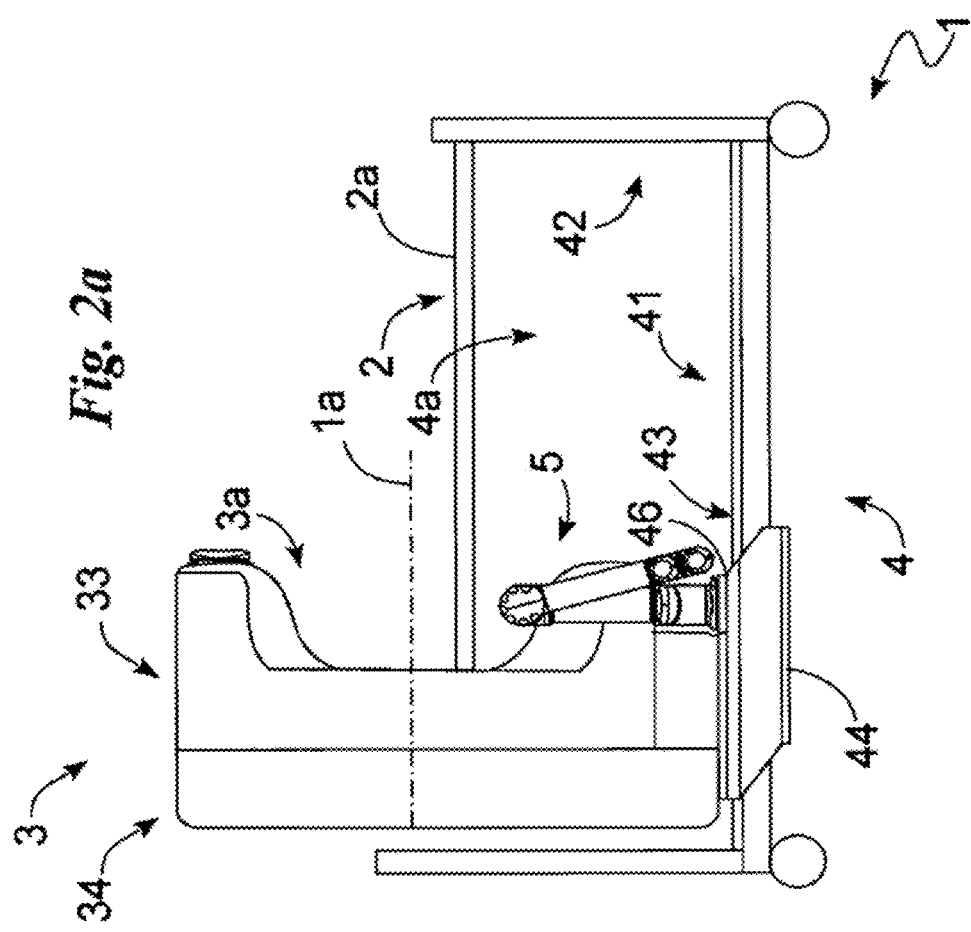

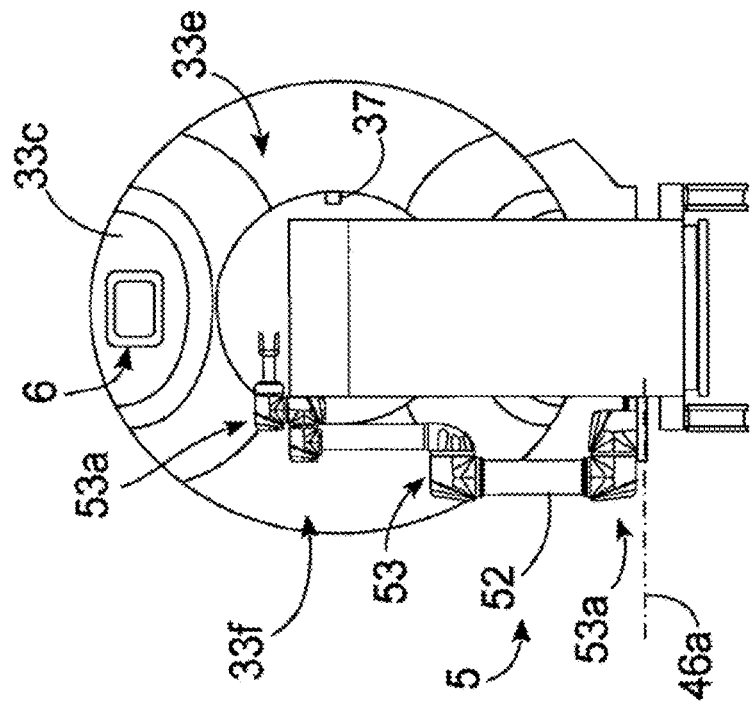
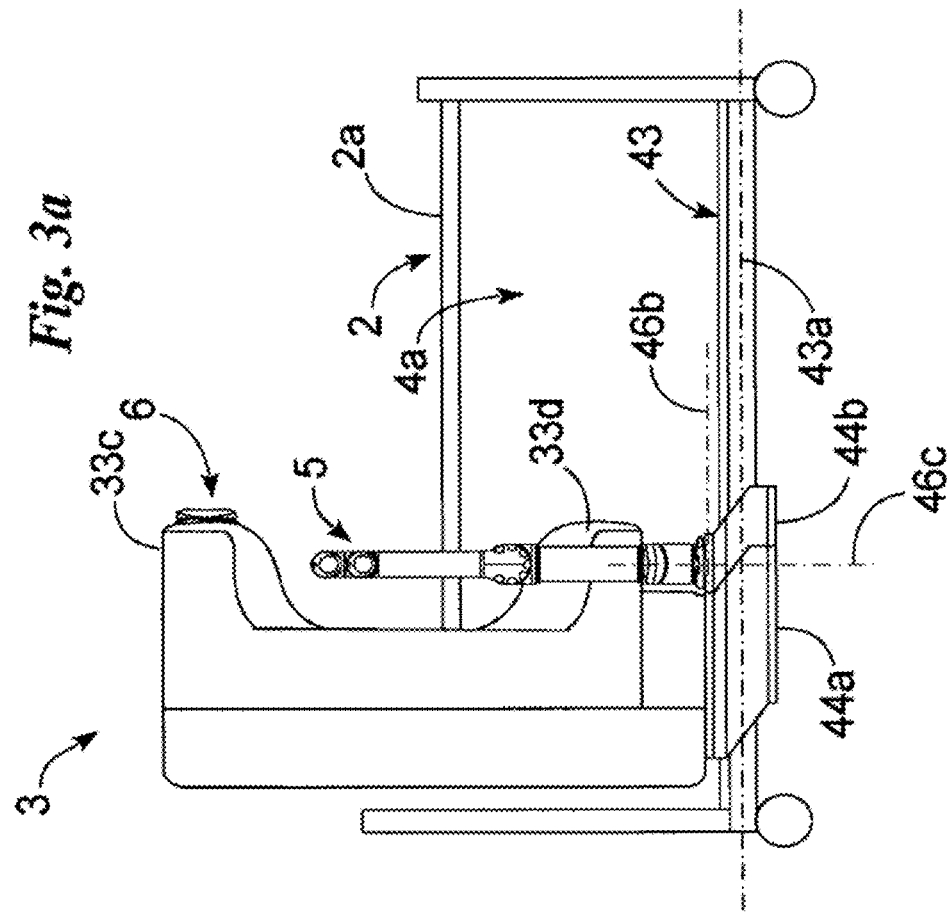

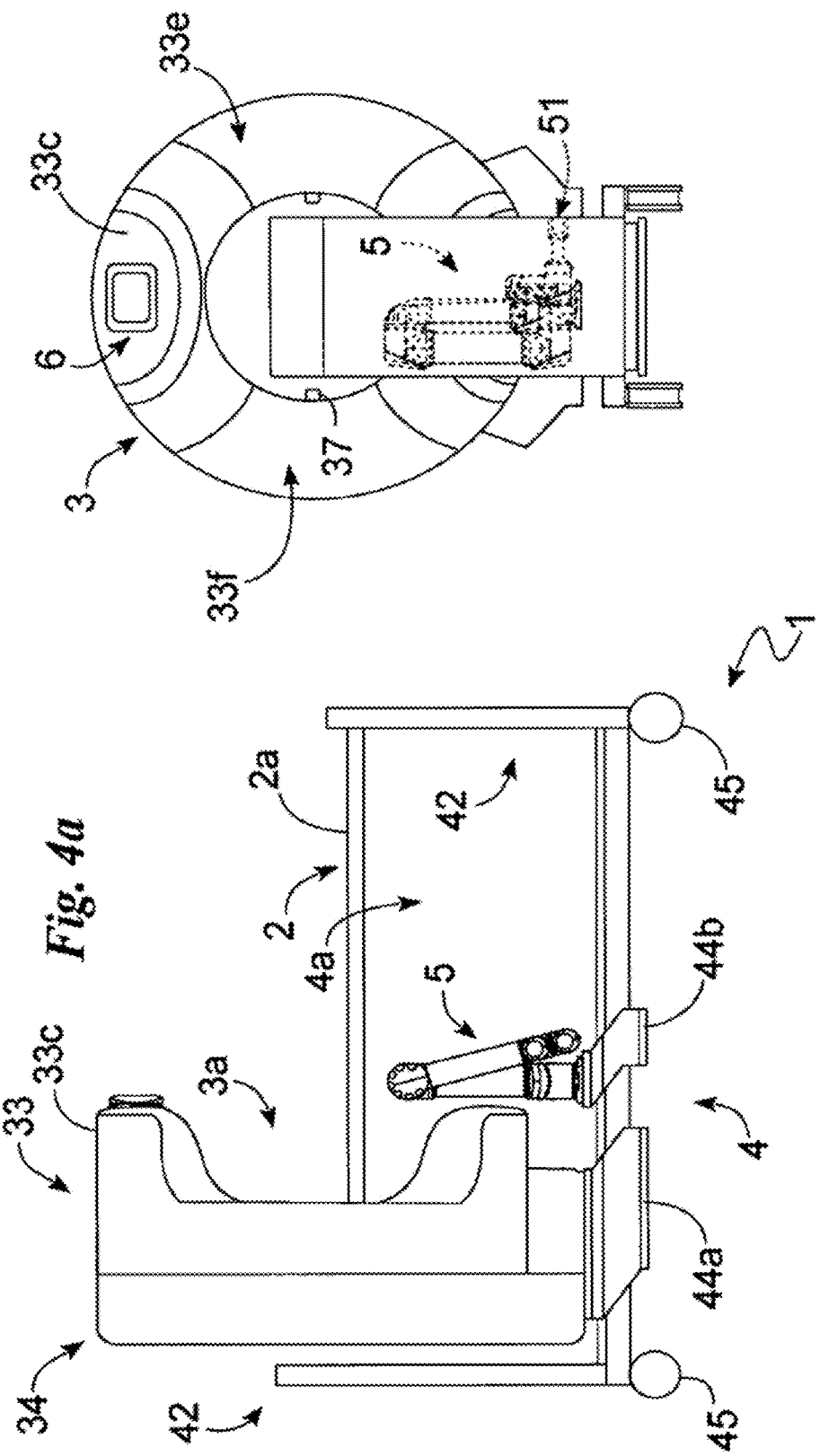

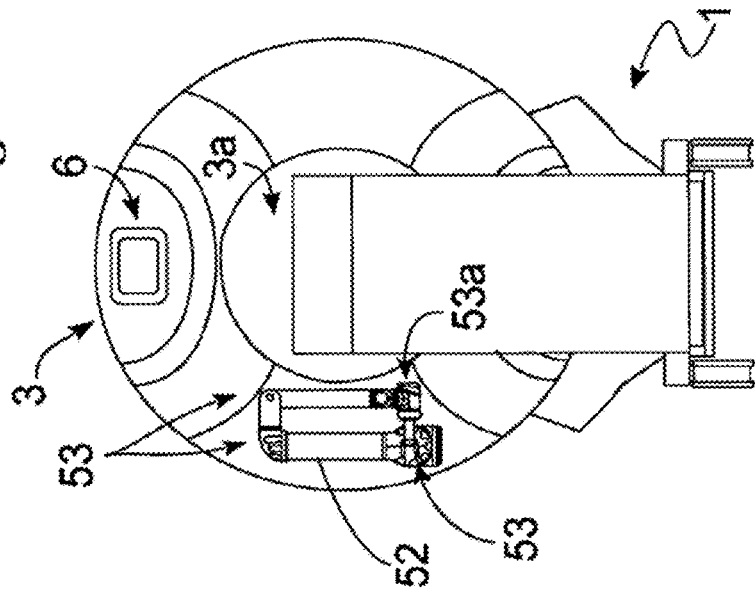
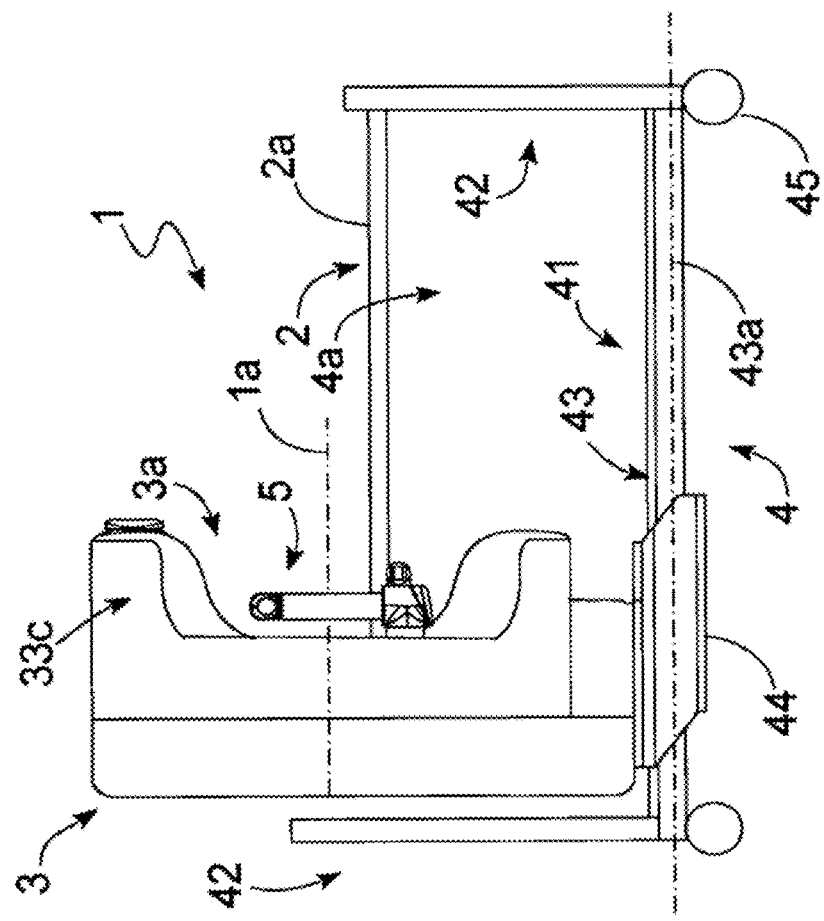

RADIOLOGICAL IMAGING DEVICE

CROSS-REFERENCE TO RELATED APPLICATIONS

This application is a continuation of U.S. application Ser. No. 16/073,773, filed Jul. 28, 2018, now U.S. Pat. No. 10,772,577, which is a National Stage Filing of International Application No. PCT/IB2017/050438, filed Jan. 27, 2017, which claims priority from Italian Patent Application Nos. UB2016A000047 and UB2016A000102, both filed Feb. 1, 2016. This application claims priority from U.S. application Ser. No. 16/073,773, International Application No. PCT/IB2017/050438, and Italian Patent Application Nos. UB2016A000047 and UB2016A000102, each of which is hereby incorporated by reference in its entirety.

FIELD OF THE INVENTION

The present invention relates to a radiological imaging device. In particular, embodiments of the invention concern devices suitable to be used in the medical/veterinary sphere to at least obtain images of at least a portion of the internal anatomy of a patient, and thus perform analyses, diagnoses or other assessments of said patient.

BACKGROUND

As known, the radiological devices currently on the market are able to perform various analyses and have a similar structure. In fact, almost all the known imaging devices comprise a bed on which to place the patient, a control station suitable to control the functioning of the device, and a gantry, that is to say a device having a cavity in which the portion to be analyzed is inserted and suitable to perform imaging of the patient. In detail, in the gantry can be identified an X-ray source, a detector that receives the X-rays after they have passed through the portion to be analyzed, and a movement system suitable to simultaneously move the source and the detector around the patient. In recent years, imaging devices have been supplemented with a robotic arm capable of helping an operator to treat the patient. In these cases, both the radiological imaging device and the robotic arm are situated inside a room and, depending on the acquisition performed by the imaging device, the robotic arm moves towards the patient and thus moves with it a medical instrument (for example a source for radiation therapy) to the body portion of the patient to be treated.

The prior art mentioned above has several significant drawbacks. A first important drawback is the complexity and difficulty of spatially relating the robotic arm and imaging device and thus controlling the relative position between the robotic arm and gantry in order to avoid impact that may damage one of the two elements. To try to solve this problem, the room is often equipped with one or more cameras that, by filming both the imaging device and the robotic arm, enable a control station to identify the relative position between the imaging device and the robotic arm. However, this solution has some important drawbacks. A first drawback is the fact that inside the room there are often operators present who, by moving around the room, obstruct the view of the cameras making it practically impossible to have a continuous control of the relative position between the robotic arm and imaging device. It is to be noted how such visual interference can also be produced by the gantry which, by moving, can come between the camera and robotic arm.

Moreover, another drawback is that, in the case of mobile radiological imaging devices, the imaging device is far from the robotic arm, which is thus unable to reach all the parts of the patient requiring the operator to move the imaging device with the patient on board. This inability of the robotic arm to reach the patient may also be determined by the operator who, assuming certain positions with respect to the bed, may prevent the robotic arm from reaching the desired position. It is also to be noted how such movement of the robotic arm may be very difficult for the operator and, above all, particularly dangerous for the patient given the presence of cannulas, drips or cables connecting the patient to medical instruments.

Another important drawback is that the operator has a limited freedom of movement on account of the presence of the gantry and, in addition, of the robotic arm which, occupying an area adjacent to that of the radiological imaging device, is a hindrance for the operator.

SUMMARY

In this situation the technical purpose of one embodiment of the present invention is to devise a radiological imaging device able to substantially overcome the drawbacks mentioned above. Within the sphere of said technical task, one important purpose of this embodiment is to have a radiological imaging device characterised by a gantry easily and uniquely spatially referable to the robotic arm in order to avoid impact between the robotic arm and parts of the device. Another important purpose of this embodiment is to provide an imaging device that allows a robotic arm to reach any point of a patient placed on the imaging device. A further purpose of this embodiment is to devise an imaging device that ensures high freedom of movement of the operator.

BRIEF DESCRIPTION OF THE DRAWINGS

The various embodiments will now be shown with the following detailed description of exemplary embodiments thereof, with reference to the accompanying drawings, in which:

FIG. 1b is a front view of the device in FIG. 1a;

FIG. 2a is a side view of the radiological imaging device in a different posture;

FIG. 2b is a front view of the device in FIG. 2a;

FIG. 3a shows a side view of another radiological imaging device according to an embodiment of the invention;

FIG. 3b is a front view of the device in FIG. 3a;

FIG. 4a shows, in a side view, the device in FIGS. 3a-3b in a different posture;

FIG. 4b is a front view of the device in FIG. 4a;

FIG. 5b is a front view of the device in FIG. 5a;

FIG. 6a shows, in a side view, the device in FIGS. 5a-5b in a different posture;

FIG. 6b is a front view of the device in FIG. 6a;

DETAILED DESCRIPTION

Figure 1B:
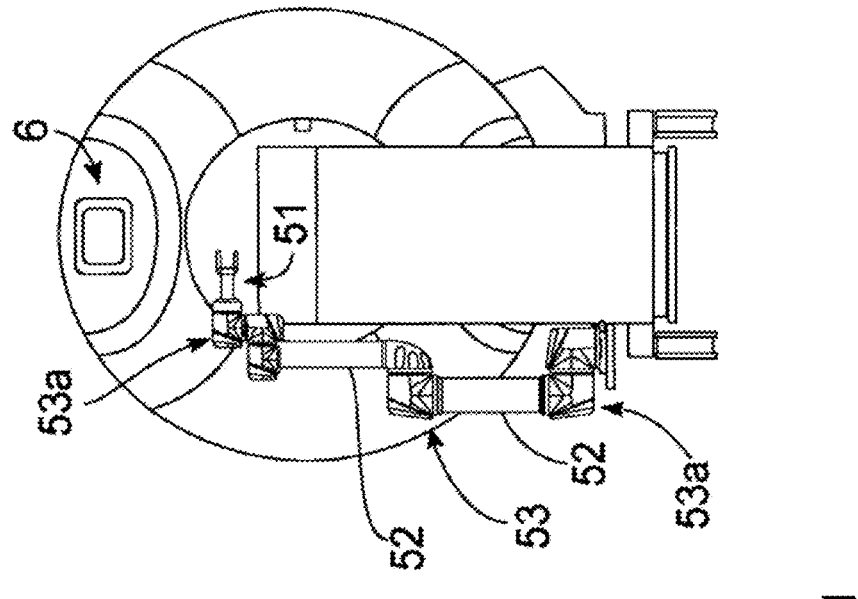
Figure 1A:
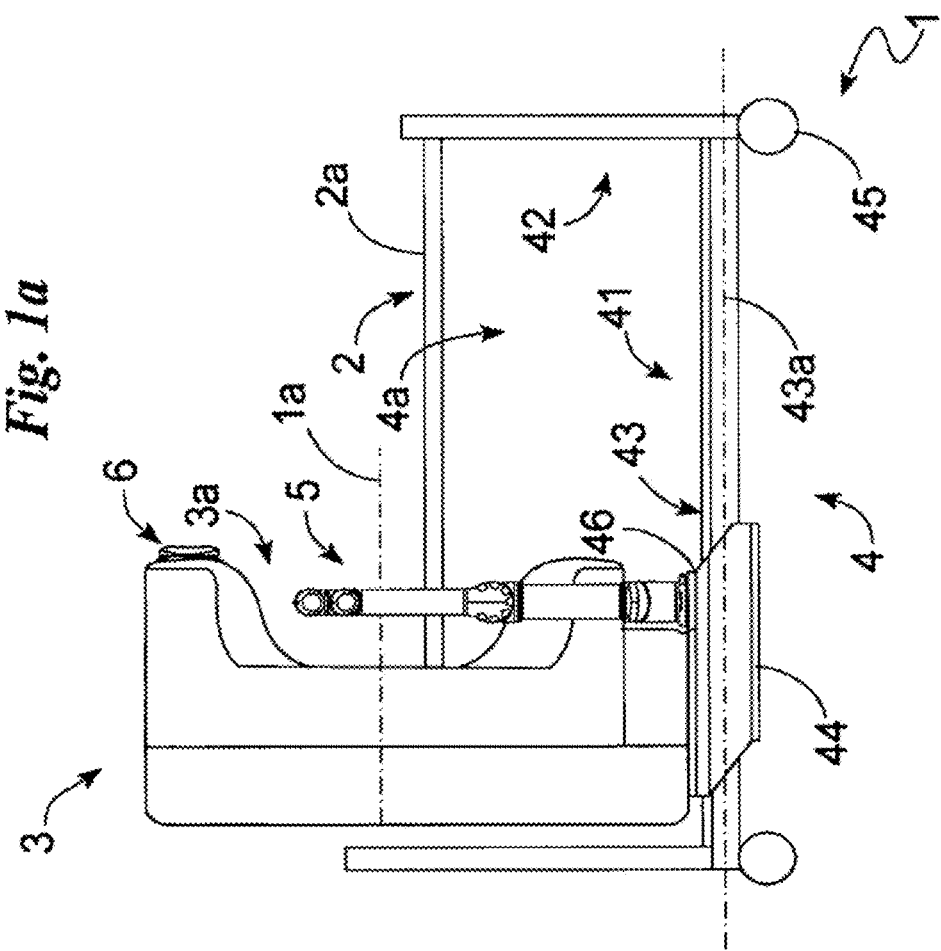
FIG. 1a shows a side view of a radiological imaging device according to an embodiment of the invention.
Figure 5B:
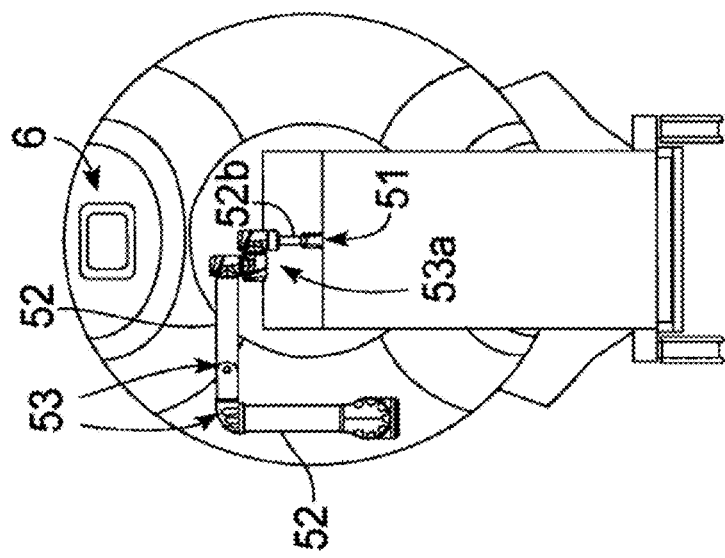
Figure 5A:
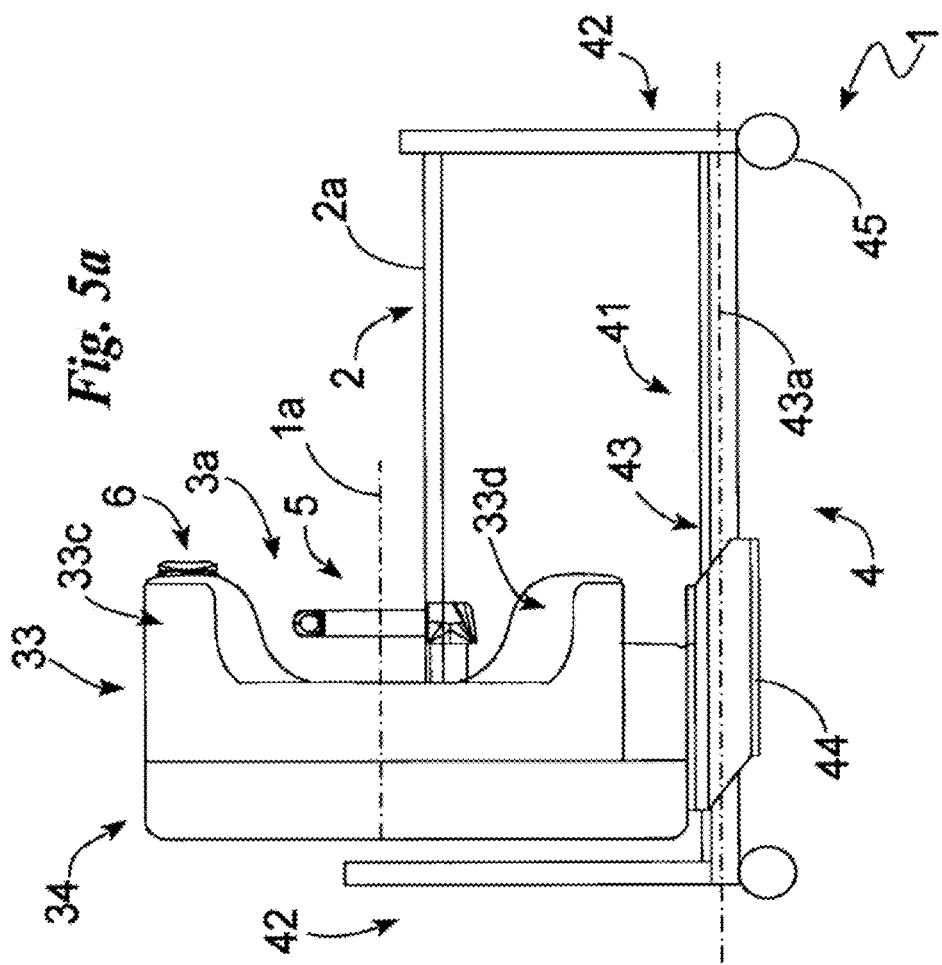
FIG. 5a shows a side view of a further radiological imaging device according to an embodiment of the invention.

Herein, the measures, values, shapes and geometric references (such as perpendicularity and parallelism), when used with words like "about" or other similar terms such as "approximately" or "substantially", are to be understood as except for measurement errors or inaccuracies due to production and/or manufacturing errors and, above all, except for a slight divergence from the value, measure, shape or geometric reference which it is associated with. For example, said terms, if associated with a value, preferably indicate a divergence of not more than 10% of said value.

In addition, where used terms such as "first", "second", "upper", "lower", "main" and "secondary" do not necessarily refer to an order, a priority relationship or relative position, but may simply be used to more clearly distinguish different components from each other.

Except where specified otherwise, as evidenced by the discussions below, consider that terms such as "processing", "computer", "computing", "evaluation", or the like refer to the action and/or a processes of a computer or calculation system which handles and/or processes data represented as physical, such as electronic magnitudes of logs of a computer system and/or memories in other data similarly represented such as physical quantities inside computer systems, logs or other information storage, transmission or display devices.

With reference to the drawings mentioned, reference numeral 1 globally denotes a radiological imaging device according to an embodiment of the invention. It is suitable for use both in the medical and veterinary spheres for performing radiological imaging of at least one portion of the internal anatomy of a patient and advantageously, medical/veterinary treatment such as for example surgery and treatment. In particular, the imaging device 1 is suitable to be used in the medical and/or veterinary sphere to perform X-rays, CT scans, fluoroscopy or other radiological examinations, surgery, therapy, or other medical and/or veterinary treatments/operations.

The radiological imaging device 1 defines a longitudinal axis 1a and comprises, principally, a bed 2 for the patient to lie on; a gantry 3 suitable to perform radiological imaging and defining an area of analysis 3a housing at least part of the bed 2; a bearing structure 4 supporting the gantry 3 and the bed 2 keeping the bed 2 in a raised position so as to preferably define a free chamber 4a; at least one robotic arm 5 suitable to move a medical instrument with respect to the area of analysis 3a and, thus, the bed 2; and a control unit suitable to control the operation of the radiological imaging device 1.

The bed 2 is substantially entirely radio-transparent and suitably made at least partially of carbon or other radio-transparent material. It is suitable to support the patient and defines an upper surface 2a for supporting a patient, i.e. a surface which in use is facing opposite to the ground. The upper surface 2a is suitable to place itself almost parallel to the longitudinal axis 1a and, in particular, to the ground.

The gantry 3 extends mainly along a circular extension trajectory lying on a main extension plane of the gantry 3 transverse and, in detail, almost perpendicular to the longitudinal axis 1a. Conveniently, the circular trajectory extension defines a main extension axis of the gantry 3 substantially coinciding with the longitudinal axis 1a. The gantry 3 is therefore almost arched with its centre lying substantially on the longitudinal axis 1a. In particular, it is C-shaped and, preferably, substantially O-shaped defining, as a result, a circular and, to be precise, substantially cylindrical area of analysis 3a. Said area of analysis 3a has its centre preferably lying on the longitudinal axis 1a.

The gantry 3 comprises a source 31 suitable to emit radiation, preferably X-rays; a detector 32 suitable to receive the radiation after it has crossed the area of analysis 3a and, therefore, the patient and the bed 2; a rotor 33 suitable to support at least the source 31 and the detector 32; a stator 34 suitable to support the rotor 33; a rotation member 35 of the rotor 33 relative to the stator 34 around the longitudinal axis 1a suitable to define a rotation trajectory of the source 31 and of the detector 32 around the area of analysis 3a and, to be precise, substantially centred on the longitudinal axis 1a; and command and control electronics of the source 31, the detector 32 and other components present on the gantry 3.

Figure 9A:
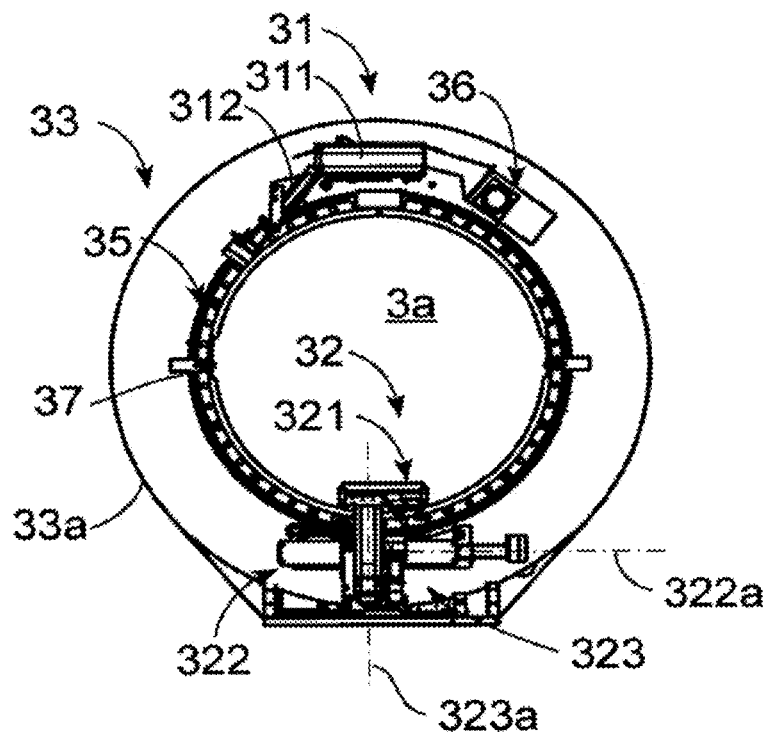
FIG. 9a shows a detail of the radiological imaging device in FIGS. 1a-4b.
Figure 9B:
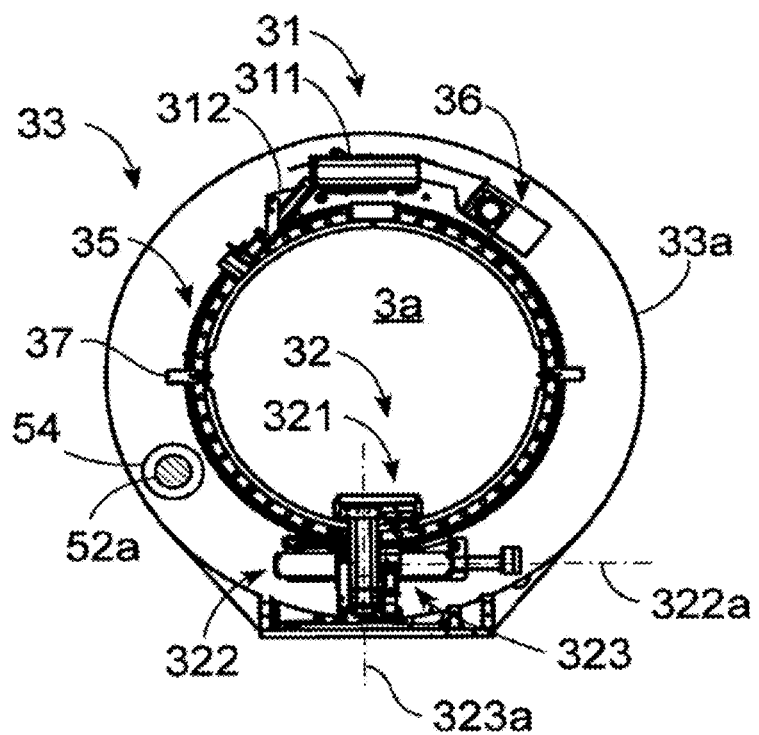
FIG. 9b shows a detail of the radiological imaging device in FIGS. 5a-6b.

The detector 32, as shown in FIGS. 9a and 9b, comprises at least one radiological sensor 321 defining a surface sensitive to X-rays and suitable to selectively perform X-rays, CT scans and/or fluoroscopy; an oscillator 322 suitable to move the radiological sensor along an oscillation axis 322a almost parallel to the sensitive surface and, suitably, almost tangent to the trajectory of rotation; and a lifting system 323 suitable to translate the radiological sensor along a lifting axis 323a almost perpendicular to the oscillation axis 322a. In particular, the lifting axis 323a is almost perpendicular and, more particularly, incident to the longitudinal axis 1a. The oscillation axis 322a is substantially parallel to the lifting axis 323a.

The radiological sensor 321 may comprise at least one of: a linear sensor and, preferably, two linear sensors defining sensitive surfaces substantially coplanar; a rectangular sensor, known as a flat panel, preferably suitable to vary the extension of the active sensitive surface, i.e. the portion of sensitive surface able to detect the X-rays; a direct photon count sensor; a dual energy sensor; a concavity sensor facing towards the longitudinal axis 1a; a variable geometry sensor: flat or concave.

The oscillator 322 comprises a slider connected to the radiological sensor 321, a waveguide defining the oscillation axis 322a and a motor, appropriately electric, controlling the movement of the slider on the waveguide. The lifting system 323 comprises a linear actuator, preferably electric, suitable to move the radiological sensor 321 and, preferably the oscillator, along the lifting axis 323a.

The source 31, as shown in FIGS. 9a and 9b, comprises an emitter 311 of X-rays defining an emission axis, and, in some cases, a tilting system 312 suitable to rotate the emitter 311 of X-rays around a tilting axis appropriately almost parallel to the longitudinal axis 1a preferably substantially keeping the focal point (focal spot) of the emitter substantially stationary. The tilting system 312 comprises a telescopic body, suitably electrically motorized, hinged at one end to the emitter 311 and at the other end to the rotor 33 so as to vary its length causing a rotation of the emitter 311 around the tilting axis and, therefore, a variation in the tilt of the emission axis with respect to the sensitive surface. The distance between the focal point and the sensitive surface is substantially between 1.4 and 0.2 m.

Figure 10:
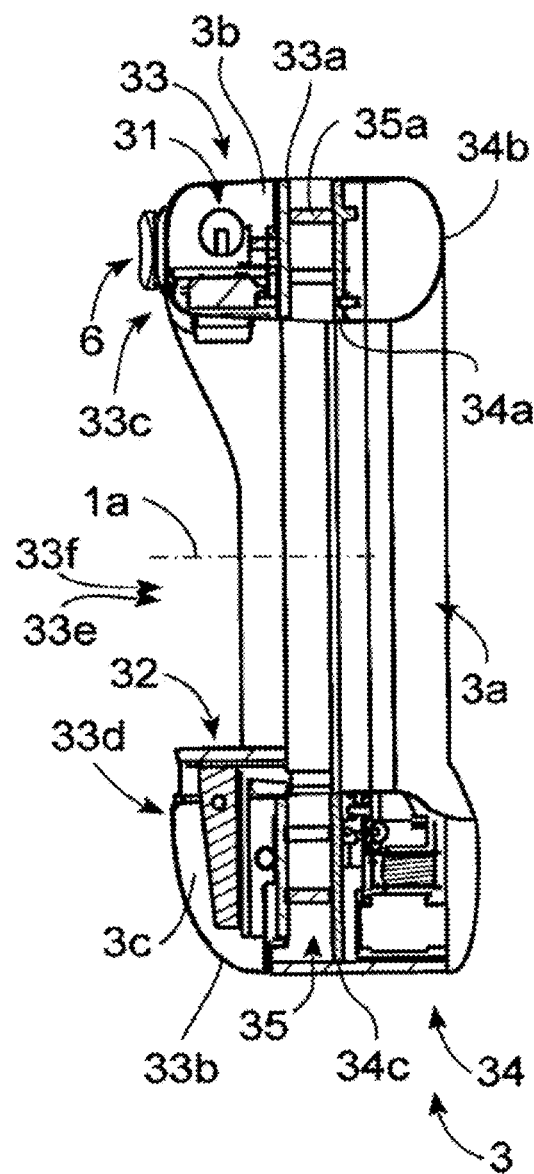
FIG. 10 shows a cross-section of an assembly of the imaging device in FIGS. 1a-4b.

The rotor 33 (FIGS. 10, 9a and 9b) comprises a rotor plate 33a to which the source 31 and, on the opposite side to the source 31 with respect to the longitudinal axis 1a, the detector 32 are connected; and a rotor casing 33b suitable to define, together with the rotor plate 33a a rotor housing volume for the source 31 and detector 32. The rotor plate 33a is suitable to support at least the source 31 and the detector 32 cantilevered. The rotor casing 33b is shaped so as to define at least one protrusion defining, together with the stator plate 33a, a housing space for the source 31 and detector 32 and at least one depression defining a profile of the rotor casing 33b and, therefore, of the rotor 33, having a lesser extension than the axial extension of the protrusion. The term "axial" identifies here, as elsewhere in the document, a distance/length/measurement calculated along the longitudinal axis 1a.

In particular, the rotor casing 33b (FIG. 10) defines a first protrusion 33c defining a first housing compartment 3b for the source 31; a second protrusion 33d opposite, with respect to the longitudinal axis 1a, to the first protrusion 33c and defining a second housing compartment 3c for the detector 32; and a first depression 33e and a second depression 33f mutually separated by the protrusions 33c and 33d and having a lesser axial extension than that of the protrusions and appropriately the same as each other.

The stator 34 (FIG. 10) is suitable to substantially support the rotor 33 cantilevered which is therefore substantially located outside the stator 34. The stator 34 comprises a stator plate 34a to which at least the control electronics of the source 31, of the detector 32 and of the other components present on the rotor 33 is connected; a stator casing 34b suitable to define, together with the stator plate 34a, a stator housing volume for the control electronics; and, suitably, a connection plate 34c to the bearing structure 4 supporting the stator plate 34a and, therefore, the stator casing 34b. Plates 33a and 34a are proximal to each other, and the casings 33b and 34b are placed on opposite sides of the plates 33a and 34a.

The rotation member 35 comprises a driven wheel integral with the rotor 33; at least one bearing suitable to allow the stator plate 34a to support the rotor plate 33a; and a motor, suitably electric and fitted with an encoder, connected to the stator plate and suitable to control, for example via a friction wheel or a belt, the rotation of the driven wheel and thus of the rotor 33.

It is to be noted how, to have a passage of data between the control electronics, located on the stator plate 34a, the source 31, the detector 32 and, if connected to the gantry 3, the robotic arm 5 and other possible components placed on the rotor plate 33a the gantry 3 comprises transfer means (such as a cable holder chain or sliding contacts) suitable to define a passage of data and/or energy between the stator 34 and rotor 33 during a reciprocal rotation; and, suitably, one or more spacers 35a suitable to be placed between the plates 33a and 34a creating a housing interspace for said transfer means.

Optionally, the gantry 3 comprises, integral with the rotor plate 33a, at least one out of a cooling system 36 of the source 31 and pointing means 37 suitable to help the operator, identifiable as the surgeon, to center the gantry 3 and, therefore, the source 31 and the detector 32 with respect to the bed 2 and, thus, the patient. Preferably, the gantry 3 comprises both the cooling system 36 and the pointing means 37. The cooling system 36 is connected cantilevered to the rotor plate 33a and placed near the source 31 and, preferably, is almost entirely housed in the first compartment 3b. The pointing means 37 comprises one or more laser emitters suitable to project onto the bed 2 and, in particular, onto the patient, optical references for centering the gantry 3. Appropriately, the pointing means 37 comprises a first laser emitter proximal to the source and suitably projecting, suitably parallel to the emission axis, a cross on the bed 2; and two additional laser emitters opposite each other and mutually tilted so as to project, suitably transversely to the emission axis, at the bed a substantially linear segment parallel to the longitudinal axis 1a. It is to be noted, lastly that only the source 31, the detector 32, cables for data/energy transmission, optionally, the robotic arm 5, as described below, and, if present, the cooling system 36 and/or the pointing means 37 are connected to the rotor plate 33a.

The robotic arm 5 is suitable to move a medical instrument, such as, for example, a radiotherapy source, a prosthesis to be implanted on the patient and/or a surgical instrument (a cannula, a scalpel, etc.) with respect to the gantry 3 and, in particular, to the bed 2. Preferably, the robotic arm 5 is suitable to move a guide body of a surgical instrument.

The expression of the guide body defines a known instrument suitable to define an intervention axis along which the operator is obliged to move a surgical instrument and, preferably, a stroke of said surgical instrument identifying the maximum depth to which the surgical instrument can be inserted in the patient. Optionally, the guide body may define an optional stroke indicating, for example, the length of cut/operation. Alternatively, the medical instrument, movable by a robotic arm 5, comprises filming means, preferably of the radiological type, suitable to allow a radiological viewing of a region of interest such as, for example, the viewing of a surgical instrument moving/operating in the area in question.

Each robotic arm 5 comprises engagement means 51 of at least one medical instrument to the robotic arm 5. The engagement means 51 are integral with the medical instrument so as to have a unique medical instrument engageable and movable by the robotic arm 5. Alternatively, the engagement means 51 are suitable to allow a change of the medical instrument so as to adapt the medical instrument to the type of surgery and/or therapy being performed. They may therefore comprise one of: a gripper able to grip or release a medical instrument; and a guide suitable to define a sliding axis and, preferably, a sliding stroke of the instrument with respect to the engagement means 51 and, thus, the robotic arm 5. It is also to be noted how, additionally, the engagement means 51 may be suitable to control and, in detail, use the medical instrument. For example, they may control the opening or closing of a clamp or by means of a suitable connection, the activation or deactivation of said filming means. The robotic arm 5 is suitable to move the engagement means 51 with respect to the gantry. To such purpose, the robotic arm 5 is articulated and formed of a kinematic chain, open or closed or partially closed.

The robotic arm 5 may comprise one or more rigid bodies 52, identifiable in sections, and one or more mechanical joints 53 suitable to move, and, to be precise, mutually rotate the rigid bodies 52. Between the rigid bodies 52, a bottom rigid body 52a suitable to connect the arm to one of said at least one carriage and the gantry and a head rigid body 52b integral with the engagement means 51 are identifiable. The mechanical joints 53 are suitable to move and, to be precise, mutually rotate the rigid bodies 52 defining, for the robotic arm 5, a retracted posture (FIGS. 2a-2b, 4a-4b, 6a-6b) in which the rigid bodies 52 are mutually juxtaposed and, consequently, the robotic arm 5 is contracted on itself placing the engagement means 51 distal to the bed 2 and, in particular, outside the area of analysis 3a, and at least one expanded posture (FIGS. 1a-1b, 3a-3b, 5a-5b) in which at least part of the rigid bodies 52 are mutually apart and, therefore, the robotic arm 5 is at least partially extended so as to place the engagement means 51 in the area of analysis 3a and, in particular, proximal to the bed 2.

In the retracted posture the rigid bodies 52 have angles of mutual divergence less than that of the expanded posture so as to have, with respect to said expanded posture minimum dimensions, calculated in the main extension plane of the gantry 3, i.e. less than the expanded posture. Therefore, in this retracted posture, the robotic arm 5 is contracted on itself so as to have minimum dimensions. To be precise, in the retracted posture the robotic arm 5 is almost entirely enclosed in the projections of the gantry 3 (FIGS. 6a-6b) and, in particular, of the rotor 33 and, more precisely, of the rotor casing 33b along the longitudinal axis 1a. Alternatively (FIGS. 2a-2b and 4a-4b), in the retracted posture the robotic arm 5 has a height, appropriately calculated perpendicular to the gravity gradient, substantially less than the height of the free chamber 4a. In the expanded posture the robotic arm 5 is at least partially extended and, thus, presents greater dimensions than said minimum dimensions.

In detail, it protrudes from said projections placing the engagement means 51 in the area of analysis 3a and suitably facing the upper surface 2a, i.e. the side opposite the base 41 with respect to the bed 2. In some cases (FIGS. 1a-1b and 3a-3b), in the expanded posture the robotic arm 5 may have a greater height than the free chamber 4a so as to reside in a depression 33e or 33f placing the engagement means 51 in the area 3a and appropriately facing the upper surface 2a, i.e. the opposite side to the base 41 with respect to the bed 2.

It is to be noted how the transition between the two postures or any other movement of the robotic arm 5 can be determined according to an indirect kinematic mechanism or a direct kinematic mechanism. It should be noted therefore that, even if not expressly stated, every movement of the robotic arm 5 described in this document is determined by the control unit according to an indirect kinematic mechanism or a direct kinematic mechanism. The expression "indirect kinematic mechanism" defines a trajectory in the operating space, i.e. the calculation of the path of the terminal member of the robotic arm 5 (identifiable by the engagement means 51 and thus the medical instrument). As a result, the control unit determines the position, speed and acceleration of the individual mechanical joints 53 so as to define said path of the terminal member of the robotic arm 5.

The expression "direct kinematic mechanism" identifies the calculation of a trajectory in the joint space in which the position, speed and acceleration of the individual mechanical joints 53 are determined rather than the path of the terminal member of the robotic arm 5. As a result, the path of the terminal member of the robotic arm 5 is not defined by the unit, but is a result of the position, speed and acceleration of the mechanical joints 53. The mechanical joints 53 are suitable to rotate independently of each other and mutually the rigid bodies 52 along at least one axis of rotation preferably almost perpendicular to the preferred extension axes of one of the two adjacent rigid bodies 52. In particular, the mechanical joints 53 are suitable to rotate independently of each other and mutually the rigid bodies 52 along two distinct axes of rotation each of which preferably almost transverse and, to be precise, almost perpendicular to a preferred extension axis of one of the adjacent rigid bodies 52. The mechanical joints 53 can be of various types, motorized or non-motorized, such as—by way of a non-limiting example—pivot joints, prismatic, spherical, helical, cylindrical or hinge joints.

Optionally, the joints 53 may be identified in variable stiffness actuators, i.e. an actuator placed between two rigid bodies 52 and/or between a rigid body 52 and the means 52 and suitable to reciprocally move the aforesaid two components, by varying the stiffness between them. An example of the variable stiffness actuator is described in paragraphs [0030]-[0088] of EP2444207 and represented in FIGS. 1-7 of said EP2444207. These pages and said drawings of the patent EP2444207 are incorporated herein by reference. Among the mechanical joints 53 a head mechanical joint 53a is placed between the head rigid body 52b and the adjacent rigid body 52. The head mechanical joint 53a is suitable to rotate the head rigid body 52b and, therefore, the engagement means 51 with respect to the rest of the robotic arm 5 around at least an axis substantially transverse and, substantially, almost perpendicular to the preferred extension axis of said adjacent rigid body 52. Preferably, the head joint 53a is suitable to rotate the engagement means 51 with respect to the rest of the robotic arm 5 along two axes almost transverse and, more preferably, perpendicular to each other. Each mechanical joint 53 and 53a comprises a servomotor, i.e. an electric motor equipped with an encoder suitable for measuring the angle of rotation between the rigid bodies 52, 52a and 52b given by said motor and to stably maintain such angle.

In order to allow the aforementioned exchange of the medical instrument moved by the robotic arm 5, the bearing structure 4 may comprise a loading station suitable to contain a plurality of medical instruments which can be picked up and, thus used by the robotic arm 5. Said loading station is housed inside the free chamber 4a and, to be precise, connected to the column 42 proximal to the robotic arm 5. Alternatively, the loading station is provided on the robotic arm 5 integral with a rigid body 52.

Figure 12:
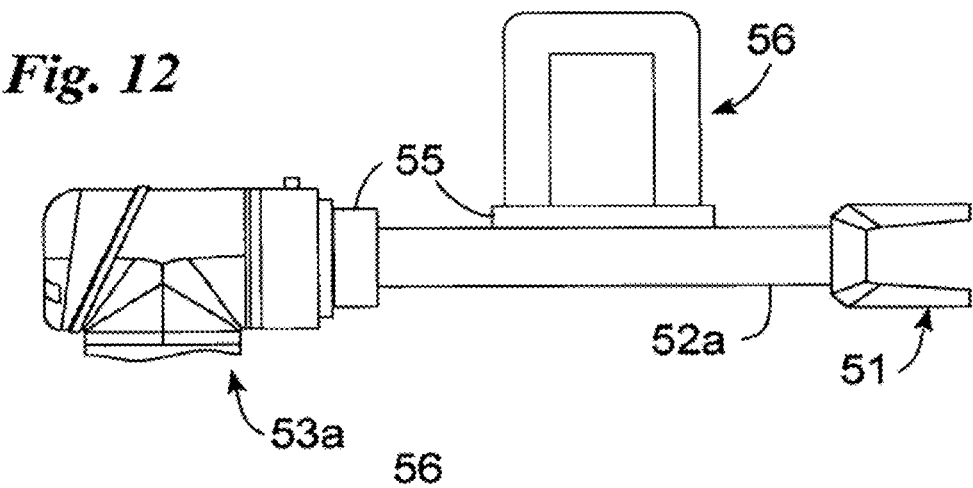
FIG. 12 is another example of the detail in FIG. 11.
Figure 13:
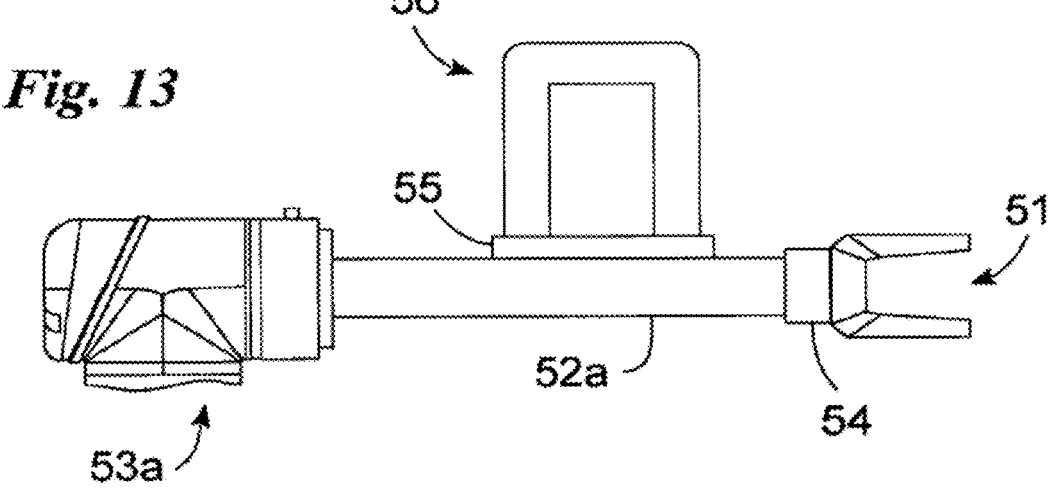
FIG. 13 shows a further example of the detail in FIG. 11.

Innovatively, the robotic arm 5 may comprise at least a force sensor 55 suitable to detect the forces/torques acting on the robotic arm 5. Said at least one force sensor 55 is, for convenience, shown only in FIGS. 11-13. The force sensor 55 is suitable to allow the engagement means 51 and, therefore, the medical instrument to be kept in the desired position with respect to the region of interest. It allows the performance of at least one of the following control modes: position/speed control, force/torque control, hybrid position/force (position on some axes and force/torque on others) control, impedance rather than force/torque control on one or more axes. It should be noted that the term "axes" identifies axes of a Cartesian tern arbitrarily defined integrally with the instrument, the engagement means 51 or the surrounding environment (e.g. patient). The force sensor 55 can measure the interaction forces/torques between the medical instrument and the identifiable surrounding environment, preferentially but not exclusively, the patient and the surgeon. In particular, it is suitable to measure the interaction forces/torques between the patient and medical instrument and, based on such, to define for the robotic arm 5 a maintenance condition in which the robotic arm 5 keeps the engagement means 51 and, thus the medical instrument in contact with the patient with a certain force/torque applied to the patient and/or a certain position. Alternatively or additionally, in the maintenance condition of the robotic arm 5 it keeps the engagement means 51 at a predetermined distance from the patient. Appropriately, the force sensor 55 is suitable to measure the interaction forces/torques of the robotic arm 5 with the surgeon and, based on such, to define for the robotic arm 5 a tracking condition in which the movements of the robotic arm 5 are substantially proportional to the forces/torques measured by the force sensor 55 and applied by the operator who is thus able to manually move the arm.

Figure 11:
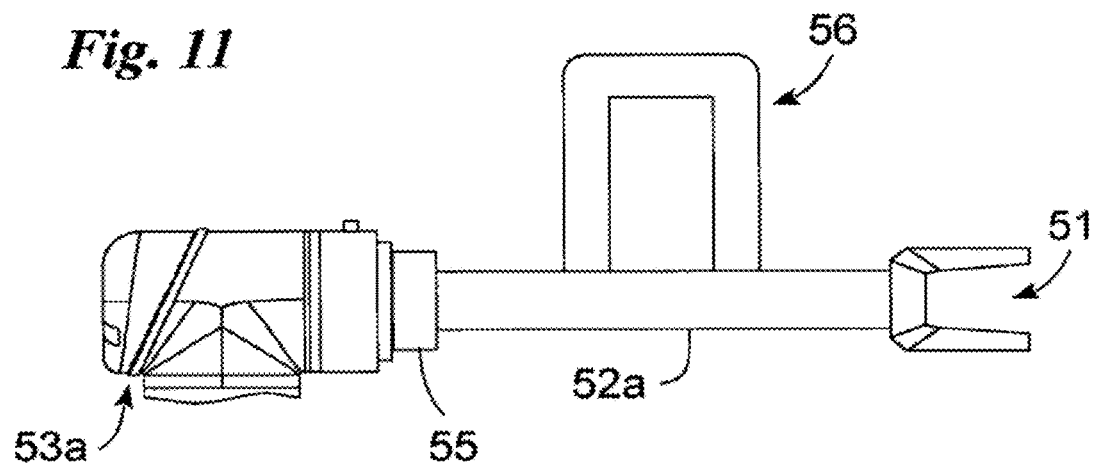
FIG. 11 shows a detail of the imaging device according to an embodiment of the invention.

It is to be noted how by using the force sensor signal 55, the control unit can allow the operator to move by rotation and/or translation, the robotic arm with respect to one or more of said axes. In some cases, the control unit can block some degrees of freedom and, therefore, allow the medical instrument to have a limited number of non-blocked degrees of freedom and, therefore, the force sensor 55 allows the execution of at least one of the above control modes only on the degrees of freedom not blocked. For example, the control unit can command the robotic arm 5 to translate exclusively along an axis proportional to the force measured by the force sensor 55 along said axis and command the robotic arm 5 to oppose forces measured by the sensor along the remaining axes and the torques calculated with respect to the three axes. Advantageously, the at least one force sensor 55 can measure the interaction forces/torques between the medical instrument and patient, or the interaction forces/torques with the surgeon, and/or a combination of said interaction forces/torques. As a result it is suitable to selectively define a maintenance condition and a tracking condition. The at least one force sensor 55 is connected to the control unit which, based on the data measured by the force sensor 55, controls the robotic arm 5 during the maintenance and the tracking condition. The transition from the maintenance to the tracking condition can be controlled by the operator and/or automatically determined by the control unit. The robotic arm 5 may comprise a single force sensor 55 suitable to measure the interaction forces/torques between the medical instrument and patient, the interaction forces/torques with the surgeon, and more appropriately a combination of said interaction forces/torques. Preferably said single force sensor 55 is interposed between the head rigid body 52b and the rest of the robotic arm 5 and, more precisely, between the head rigid body 52b and the head mechanical joint 53a (FIG. 11).

In this case, the control unit, according to a command given by the operator, commands the robotic arm 5 to activate one of the maintenance or tracking conditions. Alternatively or additionally, the unit can automatically command (i.e. without operator intervention) the robotic arm 5 to activate one of the maintenance or tracking conditions.

Preferably, the robotic arm 5 may comprise a handle 56 suitable to be grasped by the operator allowing him to move the robotic arm 5. The handle 56 is, for convenience, represented only in FIGS. 11-13. Said handle 56 is appropriately integral with the head rigid body 52b and placed downstream of the force sensor 55. The term "downstream" means that the handle is placed along the kinematic chain defined by the robotic arm 5, closer to the engagement means 51 than the force sensor 55.

Alternatively, the robotic arm 5 may comprise two force sensors 55 so that interaction forces/torques between the medical instrument and patient and interaction forces/torques with the surgeon works are measured by said two force sensors 55 independently of each other allowing the automatic recognition thereof. In this case, the control unit, being able to discriminate the interaction forces/torques between the medical instrument and patient from the interaction forces/torques with the surgeon can automatically command the robotic arm 5 to activate one out of the maintenance and tracking conditions. To have independently acting interaction forces/torques between the medical instrument and patient and interaction forces/torques with the surgeon, the two force sensors 55 are not in contact with each other. In particular, they are mutually separated by one or more rigid bodies 52, 52a and 52b, preferably by a single rigid body 52 or 52b and, more preferably, by the head rigid body 52b.

Appropriately, the robotic arm 5 may comprise a handle 56 suitable to be grasped by the operator allowing him to move the robotic arm 5. A first non-limiting example (FIG. 12) of the arrangement of the two force sensors 55 provides for a force sensor 55 placed between the handle 56 and head body 52b so as to measure almost exclusively the interaction forces/torques with the surgeon; and the other force sensor 55 placed between the head body 52b and head joint 53a so as to measure both the interaction forces/torques between the medical instrument and patient and the interaction forces/torques with the surgeon. It is to be noted how, in this example, in the case of simultaneous application of the interaction forces/torques between the medical instrument and patient and of the interaction forces/torques with the surgeon, the control unit can determine the interaction forces/torques between the medical instrument and patient based on the difference of the findings of the two force sensors 55.

A second non-limiting example (FIG. 13) of the arrangement of the two force sensors 55 provides for a force sensor 55 placed between the handle 56 and head rigid body 52b so as to measure almost exclusively the interaction forces/torques with the surgeon; and the other force sensor 55 placed between the head body 52b and engagement means 51 so as to measure almost exclusively the interaction forces/torques between the medical instrument and patient.

A third non-limiting example of the arrangement of the two force sensors 55 provides for a force sensor 55 placed between the head body 52b and head joint 53a so as to measure both the interaction forces/torques between the medical instrument and patient and the interaction forces/torques with the surgeon; and the other force sensor 55 placed between the head body 52b and engagement means 51 so as to measure almost exclusively the interaction forces/torques between the medical instrument and patient. In this case, the handle 56 and rigid head body 52b may be in one piece. It is to be noted how, in this third example (as in the first example), in the case of simultaneous application of the interaction forces/torques between the medical instrument and patient and of the interaction forces/torques with the surgeon, the control unit can determine the interaction forces/torques between the medical instrument and patient based on the difference of the findings of the two force sensors 55.

Optionally, a robotic arm 5 may comprise an additional force sensor 55 placed at the engagement means 51 so as to come into contact with the medical instrument and/or the patient. Said additional force sensor 55 is substantially similar to the force sensor 55 described above.

The bearing structure 4 comprises a base 41 suitable to support the gantry 3; at least one column 42 suitable to sustain the bed 2 in a raised position with respect to the base 41; a guide 43, suitably integral with the base 41, defining a translation axis 43a almost parallel to the longitudinal axis 1a; and at least one carriage 44 engaged to the guide 43 and suitable to move the gantry 3 and robotic arm 5 along the translation axis 43a. The guide 43 may comprise, for example, a lead screw of the translation of the at least one carriage 44 extending substantially along the translation axis 43a; and a motor, appropriately electric, commanding the rotation of the lead screw around the translation axis 43a and, thus, the movement of the at least one carriage 44 along said axis 43a. Appropriately, the structure 4 may comprise wheels 45, preferably pivoting, suitable to be positioned between the ground and the base 41 to allow the movement of the device 1.

The base 41 and at least one column 42 define the free chamber 4a. In detail, the free chamber 4a is defined underneath, i.e. in the vicinity of the ground, by the base 41; along a lateral side of the column 42; if present, along a second lateral side opposite the first side of the second column 42; and optionally above the bed 2. It consequently has two open cross-sections for access to said chamber extending almost parallel to the longitudinal axis 1a and, in particular, almost perpendicular to the upper surface 2a. The at least one carriage 44 is associated with the gantry 3 (via the connection plate 34c) and to the robotic arm 5 and engaged to the guide 43 so as to slide along it moving the gantry 3 and robotic arm 5 along the translation axis 43a.

It is to be noted that, as described further below, the robotic arm 5 can be directly connected to the at least one carriage 44 (FIGS. 1a, 1b, 2a, 2b, 3a, 3b, 4a, 4b). Alternatively (as described below), the robotic arm 5 can be connected indirectly to the at least one carriage 44 and, in particular, be connected to the gantry 3 (FIGS. 5a, 5b, 6a and 6b) which, being connected to the at least one carriage 44, joins the robotic arm 5 to the at least one carriage 44 allowing its movement along the translation axis 43a. It is noted below that the expression "directly connected", hereinafter identified uniquely by the term "connected," identifies the absence, between the components connected to each other, of further components except for what is optionally needed to achieve the connection. Conversely, the expression "indirectly connected", hereinafter identified uniquely by the term "associated," identifies the presence, between the components connected to each other, of further components in addition to those optionally needed to achieve the connection (for example in FIGS. 5a, 5b, 6a and 6b the robotic arm 5 is associated with the at least one carriage 44 in so far as the gantry 3 is between them).

In the case of the robotic arm 5 directly connected to the at least one carriage 44, the bearing structure 4 may comprise a single carriage 44 (FIGS. 1a, 1b, 2a and 2b) to which both the gantry 3 and the robotic arm 5 are connected so as to simultaneously move the gantry 3 and the robotic arm 5 along the translation axis 43a. In a second example of robotic arm 5 directly connected to the at least one carriage 44, the bearing structure 4 may comprise two carriages (FIGS. 3a, 3b, 4a and 4b), i.e. a first carriage 44a connected to the gantry 3 suitable to move the gantry 3 along the translation axis 43a and a second carriage 44b connected to the robotic arm 5 and suitable to move the robotic arm 5 along the axis 43a independently of the gantry 3. In this case, the first carriage 44a and the second carriage 44b may be suitable to slide independently of each other along the translation axis 43a and, to be precise, to be motorized. Optionally, in the case of both a single carriage 44 and of two carriages 44a and 44b, the bearing structure 4 may comprise, for each robotic arm 5, at least one mover 46, interposed between the robotic arm 5 and respective carriage 44 or 44b, suitable to move and, in particular, to at least translate, the robotic arm 5 with respect to said carriage 44 or 44b.

The mover 46 is suitable to move the robotic arm 5 along at least one of a sliding axis 46a and an approach axis 46b almost transverse, and preferably substantially perpendicular, to each other. Appropriately, the mover 46 is suitable to move the robotic arm 5 only along the sliding axis 46a or only along the approach axis 46b. Alternatively, the mover 46 is suitable to move the robotic arm 5 along the sliding axis 46a and the approach axis 46b. The sliding 46a and approach axes 46b are almost parallel to the surface 2a. The sliding axis 46a is substantially transverse and in particular perpendicular to the longitudinal axis 1a, so as to enable the mover 46 to define a parking position (FIGS. 2b and 4b) in which the robotic arm 5 is almost entirely inside the free chamber 4a; and a position of use (FIGS. 1b and 3b) in which it protrudes at least partly from the chamber 4a through one of the free faces. Preferably, the sliding axis 46a is almost horizontal, i.e. perpendicular to the gravity gradient.

Appropriately, the stroke of the mover along the sliding axis 46b is at least equal to the width of the surface 2a, calculated perpendicular to the longitudinal axis 1a, so as to have two positions of use and, thus allow the robotic arm 5 to protrude from the chamber 4a through each of the free faces. Alternatively, the device 1 may provide two arms 5 each of which next to a free face so as to face the bed 2 from opposite sides.

The approach axis 46b is substantially parallel to the longitudinal axis 1a so as to enable the mover 46 to vary, at least in the case of a single carriage 44, the distance between the rotor 33 and robotic arm 5. Preferably, the approach axis 46b is almost perpendicular to the gravitational gradient.

Optionally, the mover 46 comprises a turntable or other similar mechanism suitable to rotate the robotic arm 5 around a rotation axis 46c preferably almost perpendicular to the longitudinal axis 1a and, more preferably, almost vertical (i.e. almost parallel to the gravitational gradient). In detail, the rotation axis 46c is substantially perpendicular to the axes 46a and 46b.

Alternatively to the connection to the carriage 44 or 44b, the robotic arm 5 can be connected to the gantry 3 and, to be precise, to the rotor 33 appropriately so as to be arranged on the side opposite the stator 34 with respect to the rotor plate 33a. More preferably, the device 1 comprises at least one robotic arm 5 connected to the rotor 33 in correspondence with one of the depressions 33e and 33f and, more preferably still, two arms 5 each connected to the rotor 33 in correspondence with a depression 33e and 33f. A robotic arm 5 is integrally connected to the rotor casing 33b or preferably, integrally to the rotor plate 33a, not shown in the figure, and the rotor casing has an opening 33g through which the robotic arm 5 protrudes from the rotor casing 33b positioning itself in one of the depressions 33e and 33f.

Figure 7:
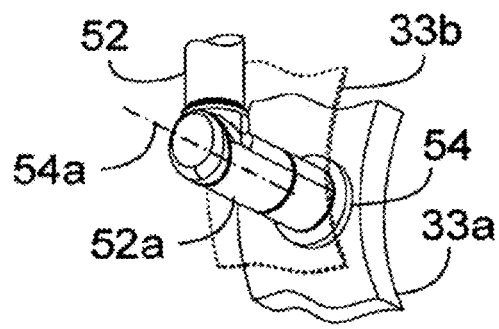
FIG. 7 shows a detail of the radiological imaging device in FIGS. 5a-6b.
Figure 8:
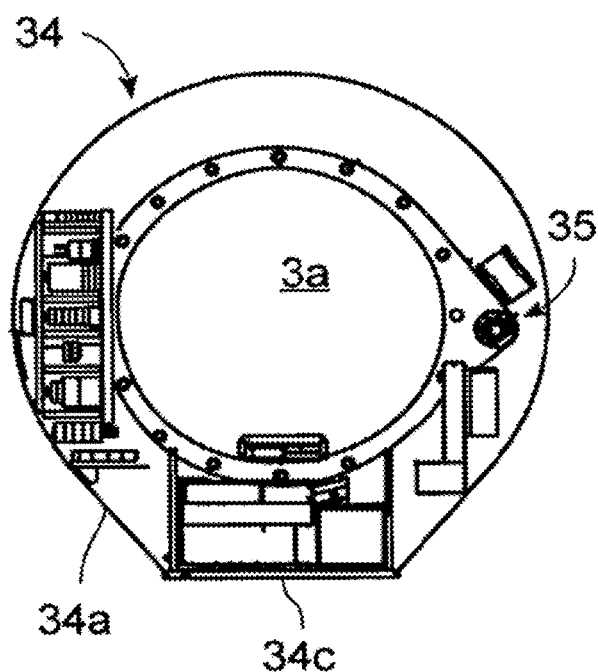
FIG. 8 schematically illustrates a cross-section of part of the radiological imaging device.

In particular, the robotic arm 5, as shown in FIGS. 7 and 9b, comprises a connection platform 54 suitable to connect the robotic arm 5 to the rotor plate 33a and, to be precise, the bottom rigid body 52a at least partly housed in the rotor volume so as to protrude from it through an opening of the rotor casing 33b. The bottom rigid body 52a has a preferred extension axis substantially transverse and, in particular, substantially perpendicular to the rotor plate and, more specifically, substantially parallel to the longitudinal axis 1a. Said connection platform 54 is preferably of the rotating type and thus defines an axis of rotation 54a of the bottom rigid body 52a and thus of the robotic arm 5. The axis of rotation 54a is almost transverse and, in particular, almost perpendicular to the rotor plate 33a and, more specifically, substantially parallel to the longitudinal axis 1a. More particularly still, the axis of rotation is substantially parallel and, to be precise, substantially coincident with the preferred axis of the bottom rigid body 52a. The rigid bodies 52 are appropriately rectilinear. Preferably one or more of the rigid bodies 52 is telescopic, i.e. suitable to vary its length. More preferably, at least the bottom rigid body 52*a* is telescopic so as to vary its extension along the preferred extension axis moving the rigid bodies 52 facing the rotor casing 33*b* with respect to said rotor casing 33*b* and the engagement means 51 along the longitudinal axis 1*a*.

The control unit is connected to the other components of the device 1 via cable and/or via a wireless connection so as to control and command the operation and movements of at least the gantry 3 and the robotic arm 5 according to a direct and/or indirect kinematic mechanism, described above. It comprises a control card suitable to automatically monitor and control the radiological imaging device 1 and interface components (touch-screen, keyboard, etc.) suitable to enable the operator to control the device 1 and, optionally, view and analyze a radiological image. In addition, the control unit comprises a front-end robot by means of which to discover and command, in every moment, the position of the medical instrument and of the robotic arm 5 in use, for example, the tilting angle both between the adjacent rigid bodies 52 and the engagement means 51 with respect to the adjacent rigid body 52 (and optionally the length of the bodies 52); and, appropriately, an instrument database through which to discover the instruments and their position in the loading station, allowing them to be picked up.

Lastly, the imaging device 1 may comprise a monitoring apparatus 6 suitable to monitor the robotic arm 5 enabling the control unit to discover the position of the individual rigid bodies 52 and, consequently, of the robotic arm 5 avoiding collisions with other objects or the operator. The monitoring apparatus 6 comprises viewing/navigation means (hereinafter solely viewing means) of the robotic arm 5 suitable to film at least the area of analysis 3*a*, i.e. the part of the bed 2 corresponding to the operating point and, therefore, the part of the patient on which to intervene with the medical instrument. In some cases, the monitoring apparatus 6 comprises one or more markers, preferably optical, suitable to spatially report an object close to the device. In detail, the monitoring apparatus 6 may comprise one or more markers integral with the robotic arm 5 and, in particular, the rigid bodies 52. Alternatively, the monitoring apparatus 6 may comprise one or more markers situated on the medical instrument so as to allow the viewing means to view and, therefore, spatially report when the medical instrument manoeuvred by the robotic arm 5 is moved and gripped by the operator. In a further alternative, the monitoring apparatus 6 may comprise one or more markers integral with the robotic arm 5 and one or more markers situated on the medical instrument.

The viewing means are connected to the rotor 33 and, in particular, to one of the protrusions 33*c* and 33*d* and, more in particular, to the top of a protrusion 33*c* and 33*d* identifiable in the surface/point of the rotor casing 33 having the maximum axial distance from the stator 34. In detail the viewing means are connected to the rotor 33 at at least one of the protrusions 33*c* and 33*d* externally to the rotor casing 33*b*, and therefore not inside the compartment 3*b* or 3*c*. Alternatively, they are placed inside the compartment 3*b* or 3*c* which is therefore preferably fitted with an optical window suitable to allow the viewing means arranged in the compartment to film at least the robotic arm 5. Preferably, the monitoring apparatus 6 comprises a single viewing means placed at the first protrusion 33*c*. Alternatively, said single viewing means is placed at the second protrusion 33*d*. In a further alternative, the apparatus 6 comprises two viewing means each placed outside or inside the protrusions 33*c* and 33*d*, at the top of the protrusions 33*c* and 33*d*. The viewing means are optical and preferably identifiable in a camera. Furthermore, the monitoring apparatus 6 may comprise, for each of the viewing means, a mover of the viewing means with respect to the rotor 33. The mover comprises at least one of: a linear actuator suitable to control a translation of the viewing means along an axis preferably substantially parallel to the longitudinal axis 1*a* and, more preferably, substantially perpendicular to the emission axis; a rotation apparatus suitable to command a rotation of the viewing means along an axis suitably almost perpendicular to the longitudinal axis 1*a* and, more suitably, to the emission axis of the source. Optionally, the mover comprises both the linear actuator and the rotation apparatus.

The functioning of the radiological imaging device described above in a structural sense is as follows. Initially, the imaging device 1 has the robotic arm 5 in the retracted posture. The operator, after placing the patient on the bed 2 and, in particular, at least partially, in the area of analysis 3*a*, commands the performance of an imaging (for example a tomography), evaluates the 3D tomographic model and views and plans the operating point and trajectory, namely the coordinates and/or the tilt that the medical instrument must adopt with respect to the patient and, thus, the bed 2. After confirming such choice, the control unit, automatically or in response to a command given by the operator, determines, based on the robot database, the trajectory to be followed to reach the desired position. For example it calculates the mutual angles between the rigid bodies 52, 52*a* and 52*b* needed to define a desired expanded posture of the robotic arm 5 enabling the positioning of the medical instrument in the operating point. It is to be noted how the path to be followed by the robotic arm 5, as well as every other movement described herein, can be determined based on a direct and/or indirect kinematic mechanism, described above.

The control unit may select the trajectory in the operating space or a trajectory in the joint space automatically or based on a command given by the operator. Appropriately, the control unit checks that the correct medical instrument associated with the engagement means 51 is present and, if necessary, orders an instrument change. In the case of an instrument change, the unit makes the carriage 44 translate, moving the robotic arm 5 towards the loading station where it deposits the instrument present on the engagement means 51 and picks up the medical instrument needed for the operation. After determining the desired expanded posture and verifying the presence of the correct medical instrument associated with the engagement means 51, the control unit orders the transition of the robotic arm 5 from the retracted posture to said desired expanded posture. Then, in the case of the arm being connected to the gantry 3, the unit orders the rotor 33 to rotate around the longitudinal axis 1*a* bringing the robotic arm 5 into the desired position.

Alternatively, in the case of a bearing structure 4 with two carriages, the control unit orders the second carriage 44*b*, in the case of a bearing structure 4 with a single carriage 44, the carriage 44, to slide along the translation axis 43*a* until the robotic arm 5 reaches the correct position. At the same time, the unit can order the gantry 3 to move a depression 33*e* or 33*f* towards the robotic arm 5 and/or the mover 46 to move the robotic arm 5 along the sliding axis 46*a* favoring the exit from the free chamber 4*a* and, thus, the reaching of the operating point by the engagement means 51. At this point, the control unit orders the passage of the robotic arm 5 from the retracted posture to the desired expanded posture, i.e. makes the mechanical joints 53 mutually rotate the rigid bodies 52 until the attainment of said reciprocal tilt angles. As a result, the robotic arm 5, guided by the unit, starts to extend towards the area of analysis 3a through one of the depressions 33e and 33f until the engagement means 51 reach the area of analysis 3a and, in particular, above the surface 2a, i.e. the operating point. The achievement of the expanded posture is completed by the head mechanical joint 53a which, by rotating the engagement means 51, places the medical instrument at the correct tilt with respect to the bed 2 and, therefore, the patient. Optionally, the control unit can order the robotic arm 5 to assume the desired expanded posture by varying, in addition to the reciprocal tilt of the rigid bodies 52, the length of one or more telescopic rigid bodies 52.

It is to be noted how the robotic arm 5 places the engagement means 51 and, consequently, the medical instrument between the protrusions 33c and 33d, i.e. between source 31 and detector 32 enabling the performance of a radiological acquisition of the engagement means 51 and the medical instrument superposed on the operating point. Such arrangement of the engagement means 51 between the protrusions 33c and 33d also enables said engagement means 51 to be visible to the apparatus 6. The movements of the robotic arm 5 are also filmed by the monitoring apparatus 6 which, filming the operating area, allows the unit to verify the position of the robotic arm 5 and, thus avoid impacts or being struck by other objects or the operator.

At this point the surgery begins. The operator picks up, for example, a scalpel, accessing the operating point from the depression 33e and 33f opposite that occupied by the robotic arm 5, inserts the medical instrument thus placing it at the desired depth and performs a cut of the desired length. Optionally, such cutting operation may be guided by the control unit which, based on the information entered by the operator, determines an operating trajectory and length and, based on such, orders a shifting of the engagement means 51 along said path. This shift is achieved by a rotation between the rigid bodies 52 and/or the rotor 33 and/or a translation of the carriage 44 or 44b.

Lastly, to improve performance of the operation, the radiological device 1 can perform, for the duration of surgery, radiological verification acquisition (preferably a fluoroscopy) which is used by the unit to follow the movements, for example due to breathing, of the operating point and take advantage of the robotic arm 5 to keep the medical instrument in the correct position despite said movements.

The radiological imaging device, described structurally and functionally above, allows an innovative method of use to be defined. Such method of use comprises a positioning step of the robotic arm 5 in a spatial position, a maintenance step of the spatial position of the medical instrument and, optionally, one or more repetition steps of the spatial positioning. The positioning step provides that the operator defines a desired position of the medical instrument with respect to the bed 2 and, therefore, the patient possibly placed on it. In this step the operator moves the robotic arm 5 by placing the medical instrument in the desired spatial position. The control unit, automatically thanks to the signals of at least one force sensor 55 or following a command given by the operator, places the robotic arm 5 in the tracking condition. To be precise, in the case of two force sensors 55, the control unit is able to distinguish the force applied to the robotic arm 5 by the operator with respect to that applied by the patient, and, thus, to place the robotic arm 5 in the tracking condition. Or, in the case of one force sensor 55, the operator reports to the unit that he is going to apply force to the robotic arm 5 so that the unit puts the robotic arm 5 in the tracking condition. Specifically, the operator applies a force to the robotic arm 5 and, in particular, to the engagement means 51 to move it. This force is detected by at least one force sensor 55 which sends a signal to the control unit which, in response to receipt of such signal, commands the robotic arm 5 to allow the movement commanded by the operator. More specifically, the at least one force sensor 55 detects for each detection axis, the force/torque components applied to the robotic arm 5, and sends these components to the control unit which allows, in each direction, a displacement proportional to said components.

Once the operator has ceased to act on the arm, the control unit, noting the absence of force by the operator places the robotic arm 5 in the maintenance condition. Alternatively, the control unit orders the passage into the maintenance condition following a command given by the operator. To be precise, in the case of two force sensors 55, the control unit is able to distinguish the force applied to the robotic arm 5 by the patient from that applied by the operator, and, thus, to place the robotic arm 5 in the maintenance condition. Or, in the case of one force sensor 55, the operator reports to the unit that he is going to stop applying force to the robotic arm 5 so that the unit puts the robotic arm 5 into the maintenance condition. Then, the control unit stores the data relative to the position of the robotic arm 5. More specifically, after completing the positioning of the robotic arm 5, i.e. when the operator does not impose any movement on the arm, the control unit blocks the robotic arm 5 and stores the data coming from at least one force sensor 55 relative to the pressure acting on it, i.e. between the patient and robotic arm 5. Alternatively, the positioning step may be performed by the control unit which, appropriately, based on the commands given by the operator orders the arrangement of the robotic arm 5 in the desired spatial position. After storing the data relative to the spatial position of the robotic arm 5 and, in particular, relative to the pressure detected by at least one force sensor 55, the positioning step is finished and the maintenance step of the spatial position starts.

In this step, the robotic arm 5 remains in the maintenance condition. The control unit now uses the data from the at least one force sensor 55 to maintain the robotic arm 5 in the correct position and, thus, the engagement means 51 and the medical instrument associated to it. In particular, the control unit imposes movements on the arm such as to keep the pressure detected by the sensor 55 substantially constant even in the presence of movements of the patient such as, for example, those due to breathing. Alternatively, the positioning step and the learning step can be performed using a medical instrument provided with markers and, preferably at least one force sensor 55 in data connection with the control unit. In this case, the positioning step provides for the operator to grip and place the medical instrument, not attached to the robotic arm 5, in the desired spatial position allowing the viewing means, using the markers on the medical instrument, to record the spatial position of the medical instrument. In addition, he may place the medical instrument in contact with the patient with a specific pressure which is detected by at least one force sensor 55 and transmitted to the control unit.

When such maintenance step is complete, the arrest step begins. In this step, the operator moves the robotic arm 5 and, thus the control unit, detecting such force thanks to the at least one force sensor 55, orders the robotic arm 5 to follow the operator during the movement away from the stored spatial position. Alternatively, the control unit, in response to a command given by the operator, imposes the return of the robotic arm 5 to the initial position. At this point, if the operator wishes to place the robotic arm 5 once again in the spatial position stored, the method of use may provide for at least one step of repeating the positioning step and the maintenance step.

In this step, the operator, by substantially and at least partially repeating the positioning step, places the robotic arm 5 and, to be precise, the engagement means 51 and, therefore, the medical instrument, in the previously stored spatial position. The control unit, thanks to the servomotors of the mechanical joints 53 and 53a and/or monitoring apparatus 6, identifies that the stored spatial position has been reached and thus commands the performance of the maintenance step. Alternatively, the position can be automatically summarised up by the robotic arm 5 in response to an appropriate command given by the operator. In this case, the control unit, using the data stored in the previous positioning step, automatically or on the basis of a command given by the operator, orders the placement of the medical instrument in the spatial position memorized and, thanks to the force sensor 55, places and keeps the medical instrument at the correct contact pressure with the patient.

Embodiments of the invention achieve some important advantages. A first important advantage lies in the fact that the robotic arm 5, being connected to one out of the carriage and gantry 3, is spatially related to said gantry 3 in an absolute and definitive manner therefore without the need for complex and laborious measuring systems external to the device. Furthermore, this aspect is further increased by the particular shape of the rotor 33 which allows the robotic arm 5 to access the area of analysis 3a through a depression 33e or 33f and, in some cases, to connect the robotic arm 5 to the rotor in a depression 33f or 33e. If, for example, the operator needs to adopt a position hampered by the robotic arm 5, the control unit, thanks to the viewing means, detects such imminent risk and imposes on the robotic arm 5 and/or the rotor 33 a shift enabling the operator to reach the position without the engagement means 51 and, thus, the medical instrument, being moved relative to the operating point. This condition is achieved by the integration of the robotic arm 5 on the device 1 and thus the presence of a control unit capable of commanding the gantry 3 and the robotic arm 5, and thus synchronizing the movements of the gantry 3 and of the robotic arm 5. It is to be noted how this advantage is increased by placing one or more markers on the medical instrument so as to enable the control unit to detect the position of the operator even when the medical instrument is moved and gripped directly by the operator without the aid of the robotic arm 5.

An important advantage is given by the innovative arrangement of the viewing means at the rotor 33 and, in particular, of a protrusion 33c and/or 33d which allows said means to film the operating point without the risk that the operator and/or other elements obstruct visibility preventing correct filming of the area. In fact, if, for example, the operator moves, obstructing the view of the viewing means, the control unit detects the impossibility of the viewing means to properly view the arm and thus commands the rotor 33 to rotate to place the viewing means in an optimal position for viewing the robotic arm 5. Such advantage is achieved by the presence of the mover which by moving the viewing means with respect to the rotor 33, ensures said viewing means an optimal view of the robotic arm 5. Furthermore, the arrangement of the viewing means in correspondence with the rotor 33 and, in particular, the protrusions 33c and/or 33d causes the robotic arm 5 and the viewing means to be spatially related to each other in an absolute and definitive manner making continuous calibrations/adjustments of their relative position superfluous. It is to be noted how this advantage is increased by placing one or more markers on the medical instrument so as to enable the control unit to detect the position of the instrument even when the medical instrument is moved and gripped directly by the operator without the aid of the robotic arm 5.

Another advantage is the fact that the robotic arm 5, being connected to the rotor 33 and, in particular, placed in a depression 33e or 33f, can easily reach all parts of the patient without imposing on the operator movements or disruptions that would slow down the operation or interfere with cables and tubes associated to the patient.

An important advantage is the fact that the imaging device 1, using the same guide 43 for moving the gantry 3 and the robotic arm 5, is very simple to construct and of reduced cost. Furthermore, the use of the same guide 43 for moving the gantry 3 and the robotic arm 5 reduces the risk of measurement errors of their position, determining a maximum precision in mutually spatially reporting the gantry 3 and robotic arm 5.

Another advantage is the fact that the robotic arm 5, being able to slide along the guide 43 staying in the free chamber 4a, can easily reach all parts of the patient without imposing on the operator movements or disruptions that would slow down the operation or interfere with cables and tubes associated with the patient.

A further important advantage, given by the presence of the depressions 33e and 33f and the particular arrangement of the robotic arm 5 and of the viewing means, is the fact that the radiological imaging device 1 provides the operator with greater freedom of movement with respect to prior devices. Furthermore, the depressions 33e and 33f allow the operator to have optimal access to the operating area and, above all, to the device 1 to perform scans to monitor in real time the position of the robotic arm 5 relative to the patient and the progress of the operation.

Another advantage of no less importance is that the arrangement of the robotic arm 5 in a depression 33e or 33f optimizes the use of space and thereby reduces the overall dimensions of the gantry with the robotic arm, facilitating transport of the device 1. In particular, such optimal use of space allows for a gantry 3 with one or two robotic arms 5 associated having substantially equal dimensions to those of the prior gantries without robotic arms.

A last advantage is given by the use of mechanical joints 53 and 53a identifiable in variable compliance actuators which make it possible to prevent the doctor or another person from hurting themselves or damaging the arm itself by bumping into the robotic arm 5. In fact, these particular actuators are able to absorb the possible impact. In addition, by being able to measure the displacement determined by the possible impact, they make it possible to restore the desired position lost after the impact.

Another important advantage is given by the method of use which, by defining one or more spatial positions easily retrievable by the operator, allows quick and easy positioning of the robotic arm 5. In fact, this method allows the device 1 to have one or more spatial positions of the robotic arm 5 which by being stored, can be obtainable without continuous control by the operator. In addition, the innovative maintenance step allows the robotic arm to compensate for the movements of the patient, for example due to breathing, and therefore have the medical instrument always in an optimal position.

Variations may be made to embodiments of the invention without departing from the scope of the inventive concept described in the claims and in the relative technical equivalents. In said sphere all the details may be replaced with equivalent elements and the materials, shapes and dimensions may be as desired. For example, the gantry 3, in place of the rotor 33 and stator 34, may be telescopic, i.e. provide a telescopic type casing and house inside it the source 31, the detector 32 and extend substantially along the extension path of the gantry 3, and house inside the housing volume at least one inner mover suitable to define a rotation of the source 31 and/or of the detector 32 around the longitudinal axis 1*a* and along the circular extension trajectory. The telescopic casing comprises an arched bottom module and an arched module movable with respect to the arched bottom module so as to vary the angular extension of the gantry along the circular extension trajectory of said gantry 3. In this case the robotic arm 5, if connected to the gantry 3, can be connected to the bottom arched module. Alternatively, the robotic arm 5 is connected to the mobile arched module.

Preferably, the device 1 may also comprise means of rotation of at least the gantry 3 around an axis of rotation substantially transverse to the longitudinal axis 1*a* and, appropriately, to the upper surface 2*a*. The means of rotation are interposed, in the case of a single carriage device, between the carriage 44 (or the first carriage 44*a*) and the gantry assembly 3 plus robotic arm 5 so as to simultaneously rotate the gantry 3 and robotic arm 5.

Such telescopic gantry 3 and, therefore, the housing of the telescopic type, the internal mover, the means of rotation of at least the gantry 3, the possible compensation member, and the optional one or more cover blocks are described from page 7, line 10, to page 26, line 22, and in the FIGS. 1a-5 of the patent MI2014A001296. These pages and said drawings of the patent MI2014A001296 are incorporated herein by reference.

The invention claimed is:

1. A radiological imaging device, comprising:
    a gantry configured to perform radiological imaging and defining an area of analysis;
    a bearing structure supporting said gantry; and
    a robotic arm configured to move a medical instrument in said area of analysis,
    wherein said bearing structure comprises:
        a guide defining a translation axis substantially parallel to a longitudinal axis of the device;
        a first carriage connected to said gantry; and
        a second carriage connected to said robotic arm, the first and second carriages moving independently of each other, said gantry and said robotic arm configured to move along said translation axis.

2. The radiological imaging device of claim 1, wherein the gantry and the robotic arm both move along the guide.

3. The radiological imaging device of claim 2, wherein the device follows the movements of an operating point due to breathing of a patient within the area of analysis and corrects a position of the medical instrument to compensate for said movements.

4. The radiological imaging device of claim 3, wherein the device is operating in fluoroscopy mode.

5. The radiological imaging device of claim 1, configured to selectively perform one or more of X-rays, CT scans, and fluoroscopy.

6. The radiological imaging device of claim 1, wherein the robotic arm is configured to reach any point of a patient placed on the imaging device.

7. A radiological imaging device, comprising:
    a gantry configured to perform radiological imaging and defining an area of analysis;
    a bearing structure supporting said gantry; and
    a robotic arm configured to move a medical instrument with respect to the area of analysis,
    wherein said bearing structure comprises:
        a guide defining a translation axis substantially parallel to a longitudinal axis of the device;
        a first carriage connected to said gantry; and
        a second carriage connected to said robotic arm, the first and second carriages moving independently of each other, said gantry and said robotic arm configured to move along said translation axis; and
    wherein the gantry is spatially referable to the robotic arm in order to avoid impact between the robotic arm and parts of the device.

8. The radiological imaging device of claim 7, further comprising a monitoring apparatus to monitor the robotic arm so as to avoid collisions with other objects or an operator of the imaging device.

9. The radiological imaging device of claim 8, wherein the monitoring apparatus is configured to film at least the area of analysis.

10. The radiological imaging device of claim 8, wherein the monitoring apparatus is configured to verify the position of the robotic arm.

11. The radiological imaging device of claim 8, wherein the monitoring apparatus comprises one or more optical markers integral with the robotic arm.

12. The radiological imaging device of claim 8, wherein the monitoring apparatus comprises one or more optical markers situated on the medical instrument.

13. The radiological imaging device of claim 8, wherein the monitoring apparatus comprises one or more optical markers integral with the robotic arm and one or more markers situated on the medical instrument.

* * * * *